(12) United States Patent
Tanimoto et al.

(10) Patent No.: US 8,318,978 B2
(45) Date of Patent: Nov. 27, 2012

(54) PROCESS FOR PRODUCING ACRYLIC ACID

(75) Inventors: Michio Tanimoto, Himeji (JP); Hideo Onodera, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 357 days.

(21) Appl. No.: 12/659,994

(22) Filed: Mar. 26, 2010

(65) Prior Publication Data

US 2010/0249454 A1    Sep. 30, 2010

(30) Foreign Application Priority Data

Mar. 26, 2009    (JP) ................ 2009-075793

(51) Int. Cl.
*C07C 51/16* (2006.01)
*C07C 45/52* (2006.01)

(52) U.S. Cl. ........................ 562/532; 568/486

(58) Field of Classification Search ............... 562/547, 562/532; 568/479, 486
See application file for complete search history.

(56) References Cited

U.S. PATENT DOCUMENTS

| 7,015,354 B2 | 3/2006 | Petzoldt et al. | |
| 7,683,220 B2 * | 3/2010 | Matsunami et al. | 568/485 |
| 2008/0228001 A1 | 9/2008 | Ogawa et al. | |

FOREIGN PATENT DOCUMENTS

| JP | 2005-336085 | 12/2005 |
| JP | 2007-502254 | 2/2007 |

* cited by examiner

*Primary Examiner* — Taylor Victor Oh
(74) *Attorney, Agent, or Firm* — Wenderoth, Lind & Ponack, L.L.P.

(57) ABSTRACT

The invention offers an improvement in a process for start-up in the occasion of producing acrylic acid by catalytically oxidizing acrolein at vapor phase under high load conditions, the start-up meaning the step of increasing the acrolein supply rate (loading) from the non-reacting condition to the prescribed reaction conditions. This process is characterized in that the acrolein supply rate is increased in the start-up stage of the reaction until the prescribed composition of starting reactant gas and the flow rate of the starting reactant gas are obtained, while adjusting at least one of the reaction temperature, the composition of the starting reactant gas and the flow rate of the starting reactant gas, so as to maintain the acrolein conversion at not lower than 90 mol %, the maximum peak temperature of the catalyst layer in each reaction zone at no higher than 400° C., and the sum of each ΔT (maximum peak temperature of a catalyst layer-reaction temperature) at the catalyst layer in each of the reaction zones to be no more than 150° C., respectively. According to this process, the reaction speedily reaches the steady state (standard operating conditions) and a high acrylic acid yield is stably achieved from the start of the reaction.

10 Claims, No Drawings

PROCESS FOR PRODUCING ACRYLIC ACID

TECHNICAL FIELD

This invention relates to a process for producing acrylic acid by catalytic vapor-phase oxidation of acrolein or an acrolein-containing gas with molecular oxygen or a molecular oxygen-containing gas, stably from beginning of the reaction with high productivity or with high yield.

BACKGROUND ART

Acrylic acid is industrially important as a starting material for various synthetic resins, paints, plasticizing agents and the like. In recent years, its importance is still increasing, as a starting material for water absorbent resins. Acrylic acid is most generally produced by two-stage oxidation method, in which propylene is catalytically oxidized at vapor phase to yield mainly acrolein, and the acrolein is successively catalytically oxidized at vapor phase to yield acrylic acid. New production methods are also proposed recently, such as acrylic acid production by catalytic vapor-phase oxidation of acrolein which is obtained by dehydration of glycerin. Acrylic acid is now produced in all the world on a scale of several millions of tons per year, and the demand therefor as a starting material of water absorbent resins continues to expand. To cope with such increasing demand, a simple and general solution is to raise the productivity of acrylic acid by increasing the load of the starting material at the steady state of the catalytic vapor-phase oxidation.

The catalytic vapor-phase oxidation of acrolein, however, is exothermic, and the calorific value also increases when the acrolein load as the starting material is increased. Besides, during the period of start-up from the non-reacting condition up to immediately after attaining the prescribed reaction conditions, the catalytic activity is unstable, and when the acrolein load is rapidly increased at the start-up, abnormal heat generation in the catalyst layer(s) is apt to occur to give rise to local heat-generating sites (hot spots), inviting in consequence reduction in the acrylic acid yield due to the high temperature reaction and deterioration of the catalyst which is exposed to the high temperature. Such problems become even more serious when the vapor-phase oxidation is carried out under high load condition.

Thus, in the method of producing acrylic acid by catalytic vapor-phase oxidation of acrolein with molecular oxygen, a process enabling the production with higher stability and higher productivity or yield is in demand, and a number of proposals have been made also about contrivances for the start-up.

For example, the following patent documents 1 and 2 disclose a method in which the supply amount per unit time of the starting material is kept low for a fixed period at the start-up stage of the reaction.

PRIOR ART

Patent Documents
  [Patent document 1] JP2005-336085A
  [Patent document 2] JP2007-502254T

SUMMARY OF THE INVENTION

Problems to be Solved by the Invention

In the process for producing acrylic acid by catalytic vapor-phase oxidation of acrolein under high load condition, during the period of start-up from the non-reacting condition until the prescribed reaction conditions are reached, the supply rate of acrolein as the starting material is raised. When the acrolein supply (load) is rapidly increased in this period, reduction in the acrylic acid yield and deterioration of the catalyst are invited as above-described.

Whereas, when the low load condition (i.e., low starting material supply rate) is continued for a long time until the prescribed reaction conditions are reached as proposed in the patent documents 1 and 2 to suppress abnormal heat generation at the catalyst layer(s), not only the acrylic acid production rate during that period drops, but also activation of the catalyst becomes insufficient and its intrinsic performance cannot be fully exhibited after the prescribed reaction conditions are reached. Hence many hours are required until the stable, high catalytic performance is achieved. Furthermore, due to the unstable catalytic activity, in certain cases deterioration of the catalyst is invited by localized heat generation.

Also many proposals are made in recent years about the production process of acrylic acid by catalytic vapor phase oxidation of acrolein using a fixed bed reactor in which catalysts are loaded in such a manner that plural reaction zones differing in catalytic activity are formed in the reaction tube(s). Where such a reactor comprising plural reaction zones is used, it is difficult to well balance the activity in each of the reaction zones during the start-up stage due to unstable catalytic activity, leading to a problem that the reaction rapidly advances at a part of the reaction zones and the catalyst in the particular zone(s) deteriorates due to the excessive heat generation.

Accordingly, therefore, the object of the present invention is to provide a start-up method whereby the steady state (standard operating conditions) of the reaction is quickly reached and a high acrylic acid yield is stably achieved from the start of the reaction with less deterioration of the catalyst, even when a reactor of which reaction tube(s) are so loaded that plural reaction zones of different catalytic activity are formed therein is used.

Means for Solving the Problems

We have engaged in concentrative studies with the view to solve above problems, to discover: in the process for producing acrylic acid by catalytic vapor-phase oxidation of acrolein or an acrolein-containing gas in the presence of molecular oxygen or a molecular oxygen-containing gas, the prescribed reaction conditions can be quickly reached and high acrylic acid yield can be obtained stably from the very start of the reaction, by carrying out the start-up of the reaction while regulating the reaction conditions so as to secure the specific prescribed state of the reaction.

Thus, according to the present invention, a process for producing acrylic acid by catalytic vapor-phase oxidation of acrolein or an acrolein-containing gas with molecular oxygen or a molecular to oxygen-containing gas, using a fixed bed reactor which is loaded with the catalysts in such a manner that at least two layers of the reaction zones having different activity are formed in the axial direction of each of the reaction tubes, is provided, which process is characterized in that the acrolein supply rate is increased in the start-up stage of the reaction until the prescribed composition of starting reactant gas and the flow rate of the starting reactant gas are attained, while adjusting at least one of the reaction temperature, the composition of the starting reactant gas and the flow rate of the starting reactant gas, so as to maintain the acrolein conversion at not lower than 90 mol %, the maximum peak temperature of the catalyst layer in each reaction zone at no higher than 400° C., and the sum of each ΔT (maximum peak temperature of a catalyst layer-reaction temperature) at the catalyst layer in each of the reaction zones to be no more than 150° C., respectively.

EFFECT OF THE INVENTION

According to the present invention as described in the above, in the occasion of producing acrylic acid by catalytic vapor-phase oxidation of acrolein or an acrolein-containing gas with molecular oxygen or a molecular oxygen-containing gas using a fixed bed reactor which is loaded with the catalysts in such a manner that at least two layers of the reaction zones having different activity are formed in the axial direction of each of the reaction tubes, the start-up can be carried out within a short time. In consequence it becomes possible to quickly attain the prescribed reaction conditions, to prevent deterioration of the catalyst due to overheat at the start-up time and, furthermore, to obtain acrylic acid stably at high yield from the start of the reaction.

EMBODIMENTS FOR CARRYING OUT THE INVENTION

Hereinafter the process for producing acrylic acid of the present invention is explained in details, it being understood that the scope of the invention is not limited by the explanation given in the following but the invention can be suitably modified and put to practice within a scope not impairing the purpose of the present invention.

The process of the present invention concerns production of acrylic acid by catalytic vapor-phase oxidation of acrolein or an acrolein-containing gas with molecular oxygen or a molecular oxygen-containing gas, using a fixed bed reactor which is loaded with the catalysts in such a manner that at least two layers of the reaction zones having different activity are formed in the axial direction of each of the reaction tubes, the process being characterized in that the acrolein supply rate is increased in the start-up stage of the reaction until the prescribed composition of the starting reactant gas and the flow rate of the starting reactant gas are attained, while adjusting at least one of the reaction temperature, the composition of the starting reactant gas and the flow rate of the starting reactant gas, so as to maintain the acrolein conversion at not lower than 90 mol %, the maximum peak temperature of the catalyst layer in each reaction zone at no higher than 400° C., and the sum of each ΔT (maximum peak temperature of a catalyst layer-reaction temperature) at the catalyst layer in each of the reaction zones to be no more than 150° C., respectively.

The catalysts useful for the present invention are subject to no particular limitation, so long as they are catalysts for production of acrylic acid by catalytic vapor-phase oxidation of acrolein or an acrolein-containing gas with molecular oxygen or a molecular oxygen-containing gas, and any of heretofore known oxide catalysts can be used. More specifically, those oxide catalysts comprising the catalytically active ingredients as represented by the following general formula (1) can be conveniently used:

$$Mo_{12}V_aW_bCu_cA_dB_eC_fD_gO_x \quad (1)$$

(wherein Mo is molybdenum, V is vanadium, W is tungsten, Cu is copper, A is at least one element selected from the group consisting of cobalt, iron, nickel, lead and bismuth, B is at least one element selected from the group consisting of antimony, niobium and tin, C is at least one element selected from the group consisting of silicon, aluminum, titanium and zirconium, D is at least one element selected from alkali metals, O is oxygen, and a, b, c, d, e, f, g and x respectively denote atomic numbers of Mo, W, Cu, A, B, C, D and 0 wherein 2≦a≦15, 0≦b≦10, 0≦c≦6, 0≦d≦30, 0≦e≦6, 0≦f≦60, 0≦g≦6, and x is a value determined according to the state of oxidation of each of the elements).

There is no particular limitation also as to the shape of the catalyst, which may be spherical, columnar, ring-formed or amorphous. Obviously, "spherical" does not mean true spheres but substantially spherical shape is satisfactory. This applies also to columnar and ring forms.

The method for preparing the catalyst is again subject to no particular limitation, and any of heretofore known methods may be used. As the molding method, extrusion molding, tabletting, Malmerizer method, granulation (tumbling granulation and centrifugal flow coating), impregnation, evaporation to dryness or the like can be adopted. While these methods can be suitably selected and used in combination, granulation method for having an optional inert carrier of a fixed shape carry the catalytically active components is preferred. More concretely, as the inert carrier, carriers having a prescribed shape made of, for example, alumina, silica, silica-alumina, titania, magnesia, steatite, silicon carbide and the like can be used.

In the present invention, it is preferred to use as the fixed bed reactor which is loaded with the catalysts in such a manner that at least two layers of the reaction zones differing in activity are formed in the axial direction of each of the reaction tubes, a fixed bed reactor which is so loaded with the catalysts that the catalytic activity in the reaction zones is successively increased from the inlet side of the reaction gas toward the exit side. As the means for varying the activity for each reaction zone, known technique can be used. For instance, dilution of the catalysts with an inert substance [JP 53 (1978)-30688B], changing the catalyst size [JP 9 (1997)-241209A], or changing the catalytically active component-carrying ratio (weight ratio of the active ingredients per catalyst) [JP 7 (1995)-10802A] have been proposed. The length of each reaction zone is suitably determined to allow the catalyst selected as above to exhibit its maximum effect. Generally the length of the catalyst-loaded reaction zone at the inlet side of the reaction gas occupies 10-80% of the total length of the catalyst layer, preferably 15-70%. The catalyst to be loaded in each reaction zone may be the same or different in composition or shape, and may be a molded catalyst formed by giving a fixed shape to the catalytic component, a carried catalyst formed of an optional inert carrier having a fixed shape and the catalytic component carried thereon, or a combination of such molded catalyst and carried catalyst. It is generally preferred to load one and same reaction zone with a molded catalyst or carried catalyst of the same composition and same shape.

The reactor useful for the present invention is subject to no particular limitation, it being satisfactory that the reactor is adapted to in-tube loading system wherein solid particles (catalyst particles, inert particles or the like) are loaded into the reaction tubes, and at least one of the reaction tube(s) is equipped with a device for measuring the temperature of solid particle layers. In industrial scale production of acrylic acid, known shell-and-tube reactor such as single reactor, tandem reactor and the like can be suitably utilized. In particular, a shell-and-tube reactor designed to serve also as a heat exchanger is advantageously used in the present invention, for controlling heat removal or heat supply. In such a shell-and-tube reactor the supply gas is introduced into the reaction tubes which are loaded with the solid particles and the reaction product (inclusive of intermediate product) is discharged. On the other hand, a heating medium (shell-side fluid) is flowed through the spaces between the tubes, exchanging heat with the reaction tubes to maintain a prescribed reaction temperature. The term, reaction temperature, as used in this specification means the heating medium temperature at the inlet into the reactor or reaction zone.

The device to be used in the reaction tube for the temperature measurement is not particularly limited, but any known device can be suitably utilized according to the purpose of use. As examples of suitable temperature measuring device, a thermocouple (thermometer) equipped with a temperature detection part for measuring the temperature in the reaction tube, resistance thermometer and the like can be named. For the "temperature measuring device" to be used in the present invention, it is satisfactory to have at least a temperature detection part, while a freely mobile type in the axial direction of the reaction tube is preferred, to enable it to detect the maximum peak temperature at the catalyst layer(s). For a shell-and-tube reactor, preferably plural reaction tubes for the measurement are provided among the bundle of reaction tubes, to grasp the temperature distribution throughout the inside of the reactor. As each $\Delta T$ (maximum peak temperature of the catalyst layer-reaction temperature) of the catalyst layer in each of the reaction zones in that case, the highest value measured in the plural reaction tubes is adopted.

The starting material for the reaction used in this invention is acrolein or an acrolein-containing gas. As such, an acrolein-containing gas obtained from, for example, catalytic vapor-phase oxidation of propylene or dehydration of glycerin can be used as it is, or after separating the acrolein to which oxygen, steam or other gas(es) are added where necessary. These gases may also be used in combination.

In the process for producing acrylic acid using acrolein or an acrolein-containing gas as the starting material and catalytically oxidizing the same at vapor phase with molecular oxygen or a molecular oxygen-containing gas, according to the present invention, the reaction conditions are subject to no particular limitation so far as they meet the purpose of the invention, and those conditions generally used for this type of reaction can be adopted. For example, in the reaction for producing acrylic acid from acrolein, a gaseous mixture of 1-15 vol %, preferably 4-12 vol %, of acrolein; 0.5-25 vol %, preferably 2-20 vol % of molecular oxygen; 0-30 vol %, preferably 0-25 vol % of steam and the balance of an inert gas such as nitrogen, is used as the starting gas which is contacted with an oxidation catalyst at a temperature range of 230-380° C., preferably 230-350° C., under the reaction pressure ranging 0.1-1.0 MPa. The present invention is particularly effective for the reaction under high acrolein load condition. That is, the invention is effective for the start-up of the reaction which is performed under the setting for the steady state (standard operating conditions) of the acrolein space velocity of at least 90 hr$^{-1}$ (STP), preferably at least 100 hr$^{-1}$ (STP). While depending more or less on the catalysts used, generally the acrolein space velocity exceeding 600 hr$^{-1}$ (STP), in many cases 300 hr$^{-1}$ (STP), is undesirable because sufficient catalytic performance cannot be exhibited due to the heat generated from the reaction.

When the starting acrolein supply is rapidly increased at the start-up stage under such high load condition, occasionally the maximum peak temperature of the catalyst layer exceeds 400° C. as the starting material supply rate reached around 85% of the prescribed steady condition, accompanying the rapid rise in the supply rate of the starting material. According to the present invention, the amount of acrolein supply is increased, while checking the temperature change in the catalyst layers and adjusting at least one factor of the reaction temperature, composition of the starting reactant gas and flow rate of the starting reactant gas, until the prescribed composition and flow rate of the starting gas are reached. In that occasion, it is necessary to so control the operation as to keep the maximum peak temperature of the catalyst layers at no higher than 400° C., and the sum of each $\Delta T$ (maximum peak temperature-reaction temperature) at the catalyst layer in each of the reaction zones, to be no more than 150° C., respectively.

Higher acrolein conversion is generally advantageous from the viewpoint of productivity, so long as it is not accompanied by drop in the acrylic acid yield due to high temperature reaction and catalyst deterioration due to exposure to high temperatures. It is recommendable to maintain the conversion of at least 90%, preferably at least 95%, inter alia, at least 97.5%, even at the start-up stage. Here the acrolein conversion and acrylic acid yield can be monitored by continuously sampling the gas at the inlet of the reactor and the gas at the outlet of the reactor and analyzing them by online gas chromatography.

In increasing the amount of the acrolein supply (load) up to the prescribed condition (target value) according to the invention, the reaction temperature, composition of the starting reactant gas and flow rate of the starting reactant gas are adjusted as follows, while monitoring the maximum peak temperature of the catalyst layers and $\Delta T$ at the catalyst layer in each reaction zone. Thus it is made possible to bring about target conditions within a short time, not adversely affecting the catalytic performance.

Adjustment of the Reaction Temperature

Where there are two reaction zones, for example, the following situation (1) or (2) can be envisioned as to $\Delta T$ at the catalyst layers. Accordingly, the maximum peak temperature of the catalyst layers and $\Delta T$ at the catalyst layer in each reaction zone are adjusted.

(1) $\Delta T$ at the first layer>$\Delta T$ at the second layer
(2) $\Delta T$ at the first layer<$\Delta T$ at the second layer Prevention of the maximum peak temperature of the catalyst layers from rising higher than 400° C. is achieved by lowering the reaction temperature in above case (1), and by raising the reaction temperature in case (2), balancing $\Delta T$ at the first layer with $\Delta T$ at the second layer. The starting material supply rate is further increased within a range not rendering the sum of $\Delta T$'s at the first layer and the second layer more than 150° C. These adjustments of the reaction temperature for the purpose of keeping the maximum peak temperature of the catalyst layers and the sum of $\Delta T$'s at the catalyst layers in the reaction zones within the prescribed ranges can be effected either under a fixed supply rate or increasing the supply rate, of the starting material.

Adjustments of the Composition and Flow Rate of the Starting Reactant Gas

While depending also on the capacity of individual oxidation apparatus or the process used, generally modification of the reaction conditions is possible to a certain extent. Hence, rise in the maximum peak temperature of the catalyst layers exceeding 400° C. can be prevented by changing the acrolein concentration, oxygen/acrolein ratio or steam concentration in the starting gas, while balancing the $\Delta T$ at the first layer with $\Delta T$ at the second layer. The starting material supply rate is further increased within a range not rendering sum of $\Delta T$'s at the first layer and the second layer more than 150° C. These adjustments of the composition of the starting reactant gas for the purpose of keeping the maximum peak temperature of the catalyst layers and the sum of $\Delta T$'s at the catalyst layers in the reaction zones within the prescribed ranges can be effected either under a fixed supply rate or increasing supply rate of the starting material.

In a shell-and-tube reactor, in occasions the reaction tubes in which ΔT's fall under the situation (1) and those in which ΔT's fall under situation (2) are present within a same reactor, particularly at the start-up time or high load reaction time, due to temperature distribution of the heating medium throughout the whole reactor or scattering in the catalyst loading. In such a case also it is sufficient to increase the acrolein supply rate until the prescribed composition and flow rate of the starting reactant gas are attained, while adjusting at least one of the reaction temperature, composition of the starting reactant gas and flow rate of the starting reactant gas, so that all of the reaction tubes for the temperature measuring should fulfill the standards set by the present invention. In that occasion, when the sum of each ΔT (maximum peak temperature of the catalyst layer-reaction temperature) at the catalyst layers in each of the reaction zones is going to exceed 150° C., the starting material supply rate cannot be further increased at that time point. When the sum of ΔT's starts to show a lowering tendency, the enhancement in the starting material supply rate can be resumed, whereby enabling to get to steady state (standard operating conditions) within a very short time.

EXAMPLES

Hereinafter the present invention is more specifically explained referring to Examples, it being understood that the invention is in no way restricted thereby. In the following, "mass parts" may be simply indicated as "parts" for the sake of convenience. The acrolein conversion and acrylic acid yield were calculated according to the following equations.

Acrolein conversion (mol %)=(mol number of reacted acrolein/mol number of supplied acrolein)×100

Acrylic acid yield (mol %)=(mol number of produced acrylic acid/mol number of supplied acrolein)×100

Example 1

Preparation of Catalyst 1

In 2500 parts of distilled water, 350 parts of ammonium paramolybdate, 58.0 parts of ammonium metavanadate and 89.2 parts of ammonium paratungstate were dissolved under heating and stirring. Separately, 59.9 parts of copper nitrate and 28.9 parts of cobalt nitrate were dissolved in 250 parts of distilled water under heating and stirring. Thus obtained two aqueous solutions were mixed, and further into which 36.1 parts of antimony trioxide and 17.2 parts of titanium dioxide were added to form a suspension. The suspension was heated, stirred and evaporated. So obtained dry matter was dried at 230° C. and pulverized to not greater than 150 μm in size to provide a catalyst powder. Into a centrifugal flow coating apparatus 1150 parts of spherical silica-alumina carrier having an average particle diameter of 5.0 mm was added, and into which the catalyst powder was gradually added together with 15 mass % of aqueous glycerin solution as the binder, as being passed through 90° C. hot air current, to have the carrier support the catalyst powder, followed by 6 hours' heat treatment at 410° C. in an atmosphere of air. Thus catalyst 1 was obtained. The supported rate of this catalyst 1 was about 32 mass %, and the composition of the metal elements excluding oxygen and the carrier was as follows:

$$Mo_{12}V_3W_2Sb_{1.5}Cu_{1.5}Ti_{1.3}Co_{0.6}.$$

Preparation of Catalyst 2

Catalyst 2 was obtained similarly to the catalyst 1, except that spherical silica-alumina carrier of 8.0 mm in the average particle diameter was used. The supported rate of the catalyst 2 was about 32 mass %.

Reactor

A reactor composed of a steel reaction tube of 3000 mm in total length and 25 mm in inner diameter, a shell for passing a heating medium therethrough and for covering the reaction tube, and a temperature measuring device comprising a thermocouple having a temperature-detection part for measuring temperature in the reaction tube, said thermocouple being freely mobile along the axial direction in the tube, was set vertically, and the temperatures of the catalyst layers were regularly monitored. From the top of the reactor the catalyst 2 and catalyst 1 were successively dropped to form the first reaction zone (a catalyst layer loaded with catalyst 2) and the second reaction zone (a catalyst layer loaded with catalyst 1), the respective layer lengths in the reaction zones being 800 mm and 2100 mm. The acrolein conversion and acrylic acid yield were monitored by continuously sampling the gas at the inlet of the reactor and that at the outlet of the reactor and analyzing them by online gas chromatography.

Oxidation

The temperature of the heating medium was maintained at 270° C., and into the catalyst-loaded reaction tube a gaseous mixture of 0.870 m³ of air (STP)/hr, 0.788 m³ of nitrogen (STP)/hr and 0.454 m³ (STP)/hr of steam was supplied from the bottom end of the reactor. Subsequently acrolein supply was started in such a manner as to attain its supply rate of 0.128 m³ (STP)/hr after 3 hours. The composition of the reactant gas at that time was: acrolein 5.7 vol %, oxygen 8.1 vol %, steam 20 vol %, and the balance of an inert gas such as nitrogen. The acrolein conversion was 99.2% and the acrylic acid yield was 93.9%. The respective maximum peak temperatures of the catalyst layers in the reaction zones were 335° C. in the first reaction zone, and 295° C. in the second reaction zone, and the sum of each ΔT at the catalyst layer in each of the reaction zones was 90° C.

Then the temperature of the heating medium was changed to 273° C. In the course of gradually increasing the acrolein supply, when the acrolein supply rate reached 0.148 m³ (STP)/hr, the maximum peak temperature of the catalyst layer in the second reaction zone was 300° C., but that in the first reaction zone rose to 380° C. and was about to exceed 400° C. Whereupon the temperature of the heating medium was changed to 268° C. Up to that time about 30 hours had passed since the initiation of acrolein supply, and the composition of the reactant gas then was: acrolein 6.5 vol %, oxygen 8.0 vol %, steam 20 vol %, and the balance of an inert gas such as nitrogen. The acrolein conversion was 97.8% and the acrylic acid yield was 92.7%. The maximum peak temperature of the catalyst layer in the first reaction zone temporarily rose to 385° C., and the sum of each ΔT at the catalyst layer in each of the reaction zones was 134° C.

Maintaining the temperature of the heating medium at 268° C., acrolein supply was then increased. When the acrolein supply rate was raised to 0.151 m³ (STP)/hr, acrolein conversion was about to drop below 90%, and after 46 hours of the operation the nitrogen flow rate was changed to 0.712 m³ (STP)/hr, temperature of the heating medium, to 270° C., and the acrolein supply was increased. At the end of 50 hours, the acrolein supply rate was 0.155 m³ (STP)/hr and the composition of the reactant gas was: acrolein 7.1 vol %, oxygen 8.3 to vol %, steam 21 vol %, and the balance of an inert gas such as nitrogen. The acrolein conversion was 97.2% and the acrylic acid yield was 92.1%, the maximum peak temperature of the catalyst layer in the first reaction zone was 355° C. and that in the second reaction zone was 320° C., and the sum of each ΔT at the catalyst layer in each of the reaction zones was 135° C.

Further increasing the acrolein supply rate up to the target value of 0.160 m³ (STP)/hr and the nitrogen flow rate, to 0.788 m³ (STP)/hr, the prescribed reaction conditions were reached and the start-up was completed. The composition of the reactant gas was: acrolein 7.1 vol %, oxygen 8.0 vol %, steam 20 vol %, and the balance of an inert gas such as nitrogen.

Throughout the start-up stage, acrolein conversion of at least 90 mol % was maintained, the maximum peak temperatures of the catalyst layers in both of the reaction zones were maintained below 400° C., and the sum of each ΔT at the catalyst layer in each of the reaction zones were maintained below 150° C.

Sixty-five (65) hours had passed from the initiation of acrolein supply when the start-up was completed. The acrolein conversion then was 98.0%, acrylic acid yield was 92.9%, temperature of the heating medium was 271° C., the respective maximum peak temperatures of the catalyst layers in the first and second reaction zones were 357° C. and 323° C., and the sum of each ΔT at the catalyst layer in each of the reaction zones was 138° C.

Thereafter the steady state (standard operating conditions) was maintained while controlling the temperature of the heating medium to keep the acrolein conversion of at least 97.5%, and the reaction was continued for 4,000 hours. After the 4000 hours passed, the temperature of the heating medium was 278° C., the respective maximum peak temperatures in the catalyst layers in the first and second reaction zones were 335° C. and 313° C., the sum of each ΔT at the catalyst layer in each of the reaction zones was 92° C., acrolein conversion was 98.7%, and the acrylic acid yield was 93.3%.

The data collected in the reaction procedure as described in Par. [0028] to Par. [0034] are shown in the following table.

| Time passed (hr) | Reaction Temp. (° C.) | Peak 1 ° C. | Peak 2 ° C. | ΔT Total ° C. | Acrolein Conversion % | Acrylic Acid Yield % | Acrolein Supply rate m³/hr | Acrolein Composition % | Air Supply Rate m³/h |
|---|---|---|---|---|---|---|---|---|---|
| 0 | 270 | | | | | | 0 | 0 | 0.870 |
| 3 | 270 | 335 | 295 | 90 | 99.2 | 93.9 | 0.128 | 5.7 | 0.870 |
| | 270 | 380 | 300 | | | | 0.148 | 6.3 | 0.870 |
| about 30 | 273→268 | 385 | 295 | 134 | 97.8 | 92.7 | 0.148 | 6.5 | 0.870 |
| | 268 | | | | | | 0.151 | 6.7 | 0.870 |
| 46 | 268→270 | | | | | | | | |
| 50 | 270 | 355 | 320 | 135 | 97.2 | 92.1 | 0.155 | 7.1 | 0.870 |
| 65 | 271 | 357 | 323 | 138 | 98.0 | 92.9 | 0.160 | 7.1 | 0.870 |
| 4000 | 278 | 335 | 313 | 92 | 98.7 | 93.3 | | | |

| Time passed (hr) | Oxygen composition % | Steam Supply rate m³/hr | Steam Composition % | Nitrogen Supply Rate m³/hr | Total Flow Rate m³/hr | Acrolein Space Velocity hr⁻¹ | Note (Corresponding Par's in Specification) |
|---|---|---|---|---|---|---|---|
| 0 | 8.6 | 0.454 | 22 | 0.788 | 2.112 | 0 | [0028] |
| 3 | 8.1 | 0.454 | 20 | 0.788 | 2.240 | 90 | |
| | 8.1 | 0.454 | 20 | 0.788 | 2.260 | 104 | [0029] |
| about 30 | 8.0 | 0.454 | 20 | 0.788 | 2.260 | 104 | |
| | 8.0 | 0.454 | 20 | 0.788 | 2.263 | 106 | [0030] |
| 46 | | | | 0.712 | | | |
| 50 | 8.3 | 0.454 | 21 | 0.712 | 2.191 | 109 | |
| 65 | 8.0 | 0.454 | 20 | 0.788 | 2.272 | 113 | [0031]→[0033] |
| 4000 | | | | | | | [0034] |

Comparative Example 1

The reaction was initiated in the manner similar to Example 1 and in the course of gradually increasing the acrolein supply, at the point of time when the acrolein supply rate reached 0.148 m³ (STP)/hr, the maximum peak temperature of the catalyst layer in the second reaction zone was 300° C. but that in the first reaction zone rose to 380° C. and was about to exceed 400° C. The acrolein supply however was maintained at the same rate, and the maximum peak temperature of the catalyst layer in the first reaction zone reached 410° C. By that time about 30 hours had passed since the initiation of acrolein supply, whereat the acrolein conversion was 98.0%, the respective maximum peak temperatures of the catalyst layers in the first and second reaction zones were 410° C. and 283° C., and the sum of each ΔT at the catalyst layers in the reaction zones was 147° C.

Thereafter the acrolein supply rate was gradually increased up to the target value of 0.160 m³ (STP)/hr similarly to Example 1 to attain the prescribed reaction conditions and the start-up was completed. By that time 80 hours had passed since the initiation of acrolein supply, and at which time the acrolein conversion was 97.9%, acrylic acid yield was 92.6%, the heating medium temperature was 273° C., the maximum peak temperatures of the catalyst layers in the first and second reaction zones were 345° C. and 340° C., respectively, and the sum of each ΔT at the catalyst layer in each of the reaction zones was 139° C.

Subsequently the steady state (standard operating conditions) was maintained while controlling the heating medium temperature to keep the acrolein conversion of at least 97.5% and the reaction was continued for 4000 hours in total. After the 4000 hours had passed, the heating medium temperature was 284° C., the maximum peak temperatures of the catalyst layers in the first and second reaction zones were 339° C. and 320° C., respectively, and the sum of each ΔT at the catalyst layer in each of the reaction zones was 91° C. The acrolein conversion was 98.4% and acrylic acid yield was 92.9%. Compared with Example 1, the rise rate of the heating medium temperature with time passage was high and the catalytic performance was low.

Comparative Example 2

The reaction was initiated in the manner similar to Example 1 and in the course of gradually increasing the acrolein supply, at the point of time when the acrolein supply rate was raised up to 0.151 m³ (STP)/hr, the acrolein conversion was about to drop below 90% but the acrolein supply rate was kept being increased. After 50 hours of the operation, the acrolein supply rate was 0.155 m³ (STP)/hr, the respective maximum peak temperatures of the catalyst layers in the first and second reaction zones were 340° C. and 320° C., the sum of each ΔT at the catalyst layer in each of the reaction zones was 124° C., the acrolein conversion was 94.6% and the acrylic acid yield was 89.6%. Thereafter the acrolein supply rate was increased up to the target value of 0.160 m³ (STP)/hr similarly to Example 1 to attain the prescribed reaction conditions and the start-up was completed. During the start-up, the temperature behaviors of the catalyst layers were unstable compared with those in Example 1 and more time was required for maintaining the respective maximum peak temperatures of the catalyst layers in the reaction zones at not higher than 400° C. and the sum of each ΔT (maximum peak temperature of catalyst layer-reaction temperature) at the catalyst layer in each of the reaction zones, at not more than 150° C. Thus 150 hours were consumed before the start-up was completed.

Example 2

Preparation of catalyst 3

In 2000 parts of distilled water, 300 parts of ammonium paramolybdate, 66.3 parts of ammonium metavanadate and 49.7 parts of ammonium paratungstate were dissolved under heating and stirring. Separately, 68.4 parts of copper nitrate was dissolved in 200 parts of distilled water under heating and stirring. Thus obtained two aqueous solutions were mixed and into which 20.6 parts of antimony trioxide and 14.7 parts of titanium dioxide were further added to provide a suspension. The suspension was heated, stirred and evaporated. So obtained dry matter was dried at 230° C. and pulverized to not greater than 150 μm in size to provide a catalyst powder. Into a centrifugal flow coating apparatus 960 parts of spherical silica-alumina carrier having an average particle diameter of 5.0 mm was added, and into which the catalyst powder was gradually added as together with 15 mass % of aqueous glycerin solution as a binder, as being passed through 90° C. hot air current, to have the carrier support the catalyst powder, followed by 6 hours' heat treatment at 400° C. in an atmosphere of air. Thus catalyst 3 was obtained. The supported rate of this catalyst 3 was about 31 mass %, and the composition of the metal elements excluding oxygen and the carrier was as follows:

$$Mo_{12}V_4W_{1.3}Sb_{1.0}Cu_{2.0}Ti_{1.3}.$$

Preparation of Catalyst 4

Catalyst 4 was obtained similarly to catalyst 3, except that spherical silica-alumina carrier of 8.0 mm in the average particle diameter was used. The carrying ratio of the catalyst 4 was about 31 mass %.

Reactor

Into a reactor composed of 24 steel reaction tubes of each 3000 mm in total length and 25 mm in inner diameter and a shell which covered them and through which the heating medium was passed, the catalyst 4 and catalyst 3 were successively dropped from the top of the reactor to form the first reaction zone (the catalyst layer loaded with catalyst 4) and the second reaction zone (the catalyst layer loaded with catalyst 3). The respective lengths of the catalyst layers in the reaction zones were 800 mm and 2100 mm. A temperature measuring device comprising a thermocouple having a temperature detection part for measuring the temperature inside the reaction tube and being adapted to freely move along the axial direction in the reaction tube, was installed on six of the reaction tubes, to constantly monitor the catalyst layer temperatures. The acrolein conversion and acrylic acid yield were monitored by continuously sampling the gas at the inlet of the reactor and that at the outlet of the reactor and analyzing them by online gas chromatography.

[Oxidation]

Maintaining the temperature of the heating medium at 267° C., into the catalyst-loaded reaction tubes a gaseous mixture of 20.9 m³ (STP)/hr of air, 21.9 m³ (STP)/hr of nitrogen and 8.2 m³ (STP)/hr of steam was supplied. Subsequently acrolein supply was started in such a manner as to attain its supply rate of 3.1 m³ (STP)/hr after 4 hours. The composition of the reactant gas at that time was: acrolein 5.7 vol %, oxygen 8.1 vol %, steam 15 vol %, and the balance of an inert gas such as nitrogen. The acrolein conversion was 99.2% and the acrylic acid yield was 93.7%. The respective maximum peak temperatures of the catalyst layers in the reaction zones were 318° C. in the first reaction zone, and 306° C. in the second reaction zone, and the sum of each ΔT at the catalyst layer in each of the reaction zones was 90° C.

Then the temperature of the heating medium was changed to 268° C. In the course of gradually increasing the acrolein supply, when the acrolein supply rate reached 3.4 m³ (STP)/hr, in some of the reaction tubes the maximum peak temperature in the second reaction zones rose up to 331° C., and the sum of each ΔT in the catalyst layer in each of the reaction zones temporarily rose to 143° C. and was about to exceed 150° C. Whereupon the heating medium temperature was changed to 270° C. By that time about 50 hours had passed since the initiation of acrolein supply. The composition of the reactant gas then was: acrolein 6.3 vol %, oxygen 8.0 vol %, steam 15.1 vol %, and the balance of an inert gas such as nitrogen. The acrolein conversion was 98.6% and acrylic acid yield was 93.2%. The maximum peak temperature in the second reaction zone was 333° C., and that in the first reaction zone was 350° C.

Then the heating medium temperature was changed to 269° C. and the acrolein supply rate was raised to 3.5 m$^3$ (STP)/hr. At 80 hours after the initiation of acrolein supply, the maximum peak temperature of the catalyst layer was 350° C. and the sum of each ΔT at the catalyst layer of each of the reaction zones was 137° C. Further increasing the acrolein supply rate to the target value of 3.6 m$^3$ (STP)/hr, the prescribed reaction conditions were reached and the start-up was completed. During the start-up stage, the acrolein conversion was maintained at not lower than 95 mol %, the maximum peak temperature of the catalyst layer in each of the reaction zones was kept at not higher than 390° C. and the sum of each ΔT at the catalyst layer in each of the reaction zones, not more than 150° C. By the time of the start-up completion, 100 hours had passed since the initiation of acrolein supply, at which time the heating medium temperature was 268° C. and the composition of the reactant gas was: acrolein 6.6 vol %, oxygen 8.0 vol %, steam 15 vol % and the balance of an inert gas such as nitrogen. The acrolein conversion was 98.3%, acrylic acid yield was 92.9%, the respective maximum peak temperatures of the catalyst layers in the first reaction zone and the second reaction zone were 349° C. and 322° C., and the sum of each ΔT at the catalyst layer in each of the reaction zones was 135° C.

Comparative Example 3

The reaction was initiated in the manner similar to Example 2 and in the course of increasing the acrolein supply, at the point of time when the acrolein supply rate was raised to 3.4 m$^3$ (STP)/hr, the maximum peak temperature of the catalyst layers in the second reaction zones rose to 335° C. in some of the reaction tubes. The acrolein supply however was maintained at the same rate and consequently the sum of each ΔT at the catalyst layer in each of the reaction zones got to 158° C. By that time about 50 hours had passed since the initiation of acrolein supply, whereat the maximum peak temperature in the second reaction zones was 346° C., and that in the first reaction zones was 348° C. Thereafter the acrolein supply rate was gradually increased up to the target value of 3.6 m$^3$ (STP)/hr similarly to Example 2 to attain the prescribed reaction conditions and the start-up was completed. By that time 120 hours had passed since the initiation of acrolein supply. The heating medium temperature then was 268° C., the maximum peak temperature of the catalyst layers was 349° C. and the sum of each ΔT at the catalyst layer in each of the reaction zones was 143° C. The acrolein conversion was 98.2% and acrylic acid yield was 92.1%.

Compared with Example 2, in this Comparative Example 3 the catalytic performance at the time when the prescribed reaction conditions were reached was low.

Example 3

Reactor

A reactor composed of a steel reaction tube of 3000 mm in total length and 25 mm in inner diameter, a shell for passing a heating medium therethrough and for covering the reaction tube, and a temperature measuring device comprising a thermocouple having a temperature-detection part for measuring temperature in the reaction tube, said thermocouple being freely mobile along the axial direction in the tube, was set vertically, and the temperatures of the catalyst layers were regularly monitored. From the top of the reactor the catalyst 2, catalyst 4 and catalyst 1 were dropped by the order stated, to form the first reaction zone (a catalyst layer loaded with catalyst 2), the second reaction zone (a catalyst layer loaded with catalyst 4) and the third reaction zone (a catalyst layer loaded with catalyst 1). The respective layer lengths were 150 mm, 700 mm and 2100 mm. The acrolein conversion and acrylic acid yield were monitored by continuously sampling the gas at the inlet of the reactor and that at the outlet of the reactor and analyzing them by online gas chromatography.

[Oxidation]

The temperature of the heating medium was maintained at 271° C., and into the catalyst-loaded reaction tube a gaseous mixture of 0.87 m$^3$ of air (STP)/hr, 0.87 m$^3$ of nitrogen (STP)/hr and 0.42 m$^3$ (STP)/hr of steam was supplied from the bottom end of the reactor. Subsequently acrolein supply was started in such a manner as to attain its supply rate of 0.131 m$^3$ (STP)hr after 3 hours. The composition of the reactant gas at that time was: acrolein 5.7 vol %, oxygen 7.9 vol %, steam 18.3 vol % and the balance of an inert gas such as nitrogen. The acrolein conversion was 99.1% and acrylic acid yield was 93.8%. The respective maximum peak temperatures of the catalyst layers in the reaction zones were 280° C. in the first reaction zone, 331° C. in the second reaction zone, and 294° C. in the third reaction zone, and the sum of each ΔT at the catalyst layer in each of the reaction zones was 92° C.

Then the temperature of the heating medium was changed to 273° C. In the course of gradually increasing the acrolein supply, when the acrolein supply rate reached 0.151 m$^3$ (STP)/hr, the respective maximum peak temperatures of the catalyst layers in the first and third reaction zones were 284° C. and 298° C. Whereas, the maximum peak temperature of the catalyst layer in the second reaction zone rose to 380° C. and was about to exceed 400° C., and the heating medium temperature was changed to 269° C. Up to that time about 30 hours had passed since the initiation of acrolein supply, and the composition of the reactant gas then was: acrolein 6.5 vol %, oxygen 7.8 vol %, steam 18.1 vol %, and the balance of an inert gas such as nitrogen. The acrolein conversion was 97.8% and the acrylic acid yield was 92.6%. The maximum peak temperature of the catalyst layer in the second reaction zone temporarily rose to 383° C., and the sum of each ΔT at the catalyst layer in each of the reaction zones was 143° C.

In the course of gradually increasing the acrolein supply rate while keeping the heating medium temperature of 269° C., at the point when it reached 0.154 m$^3$ (STP)/hr the acrolein conversion was about to drop below 90%. Accordingly, after 45 hours from the initiation of acrolein supply, the nitrogen flow rate was changed to 0.72 m$^3$ (STP)/hr and the heating medium temperature was raised to 271° C. to increase the acrolein supply. The acrolein supply rate after the time passage of 50 hours was 0.158 m$^3$ (STP)/hr, the composition of the reactant gas was: acrolein 7.3 vol %, oxygen 8.3 vol %, steam 19.2 vol % and the balance of an inert gas such as nitrogen, the acrolein conversion was 97.5%, the acrylic acid yield was 92.1%, the respective maximum peak temperatures of the catalyst layers were 283° C. in the first reaction zone, 352° C. in the second reaction zone and 318° C. in the third reaction zone, and the sum of each ΔT at the catalyst layer in each of the reaction zones was 140° C.

Further increasing the acrolein supply rate up to the target value of 0.164 m$^3$ (STP)/hr, the prescribed reaction conditions were reached to complete the start-up. The composition of the reactant gas then was: acrolein 7.1 vol %, oxygen 7.8 vol %, steam 18 vol % and the balance of an inert gas such as nitrogen.

Throughout the start-up stage, acrolein conversion of at least 90 mol % was maintained, the maximum peak temperatures of the catalyst layers in all of the reaction zones were maintained below 400° C., and the sum of each ΔT at the catalyst layer in each of the reaction zones, below 150° C.

By the completion of the start-up, 63 hours had passed since the initiation of acrolein supply, whereat the acrolein conversion was 98.0%, acrylic acid yield was 92.8%, heating medium temperature was 272° C., and the respective maximum peak temperatures of the catalyst layers in the first to third reaction zones were 285° C., 354° C. and 319° C. The sum of each ΔT at the catalyst layer in each of the reaction zones was 142° C.

The invention claimed is:

1. A process for producing acrylic acid by catalytic vapor-phase oxidation of acrolein or an acrolein-containing gas with molecular oxygen or a molecular oxygen-containing gas, using a fixed bed reactor which is loaded with the catalysts in such a manner that at least two layers of the reaction zones having different activity are formed in the axial direction of each of the reaction tubes, the process being characterized in that the acrolein supply rate is increased in the start-up stage of the reaction until the prescribed composition of the starting reactant gas and the flow rate of the starting reactant gas are obtained, while adjusting at least one of the reaction temperature, the composition of the starting reactant gas and the flow rate of the starting reactant gas, so as to maintain the acrolein conversion at not lower than 90 mol %, the maximum peak temperature of the catalyst layer in each reaction zone at no higher than 400° C., and the sum of each ΔT (maximum peak temperature of a catalyst layer—reaction temperature) at the catalyst layer in each of the reaction zones to be no more than 150° C., respectively.

2. The process according to claim 1, wherein the fixed bed reactor is loaded with the catalysts in such a manner that the catalytic activity in the reaction zones successively rises from a starting gas inlet side toward an outlet side.

3. The process according to claim 1, wherein the catalytic vapor-phase oxidation is carried out at an acrolein space velocity of at least 90 $hr^{-1}$ (STP) under a steady state.

4. The process according to claim 1, wherein the acrolein or acrolein-containing gas is obtained by catalytic vapor-phase oxidation of propylene with molecular oxygen or a molecular oxygen-containing gas.

5. The process according to claim 1, wherein the acrolein or acrolein-containing gas is obtained by dehydration of glycerin.

6. The process according to claim 2, wherein the catalytic vapor-phase oxidation is carried out at an acrolein space velocity of at least 90 $hr^{-1}$ (STP) under a steady state.

7. The process according to claim 2, in which the acrolein or acrolein-containing gas is obtained by catalytic vapor-phase oxidation of propylene with molecular oxygen or a molecular oxygen-containing gas.

8. The process according to claim 3, wherein the acrolein or acrolein-containing gas is obtained by catalytic vapor-phase oxidation of propylene with molecular oxygen or a molecular oxygen-containing gas.

9. The process according to claim 2, wherein the acrolein or acrolein-containing gas is obtained by dehydration of glycerin.

10. The process according to claim 3, wherein the acrolein or acrolein-containing gas is obtained by dehydration of glycerin.

* * * * *